United States Patent [19]
Potts

[11] 4,149,950
[45] Apr. 17, 1979

[54] FLOW-THROUGH IONIC TEST CELL
[75] Inventor: John R. Potts, Peekskill, N.Y.
[73] Assignee: Technicon Instruments Corporation, Tarrytown, N.Y.
[21] Appl. No.: 931,699
[22] Filed: Aug. 7, 1978
[51] Int. Cl.² ...................... G01N 27/36; G01N 27/56
[52] U.S. Cl. ............................... 204/195 G; 204/1 T; 204/195 R; 204/195 F
[58] Field of Search ........... 204/195 G, 195 F, 195 R, 204/1 H; 324/30 R

[56] References Cited
U.S. PATENT DOCUMENTS

| 3,649,504 | 3/1972 | Evans et al. | 204/195 R |
| 3,732,159 | 5/1973 | Platt | 204/195 R |

Primary Examiner—Howard S. Williams
Attorney, Agent, or Firm—S. P. Tedesco; Robert S. Salzman

[57] ABSTRACT

A flow-through test cell is disclosed which features an electrical conductor disposed in non-contacting adjacency with an ionic sensing electrode and a porous liquid junction for improving signal-to-noise ratio. The electrical conductor provides a low-impedance path through the fluid which effectively neutralizes signal distortion due to impedance variations in the air-segmented, continuously flowing stream. The electrical conductor includes distended sections which fixedly position such conductor in the ionic test cell, whereby shorting contact with said ionic sensing electrode and said porous liquid junction element is prevented.

21 Claims, 4 Drawing Figures

FLOW-THROUGH IONIC TEST CELL

FIELD OF THE INVENTION

This invention pertains to flow-through ionic test cells and, more particularly, to a low-impedance shunt disposed within such test cell for improving the signal-to-noise ratio.

BACKGROUND OF THE INVENTION

Heretofore, it has been known to utilize flow-through cells for the ionic or pH measurement of aqueous solutions as described in the article, "Theoretical and Practical Aspects of Ion-Selective Electrodes in Continuous-Flow Systems", by John R. Potts, *ADVANCES IN AUTOMATED ANALYSIS*, Vol. 3, Technicon International Congress, 1976, Mediad, Inc., Tarrytown, N.Y. 10591. This type of test cell lends itself nicely to measurement of the ionic or pH values for solutions because the high flow rate generally provides adequate mixing on the sensing elements, so as to achieve reproducible and accurate measurements. To achieve reproducible and accurate measurements with limited amounts of sample at high processing rates, however, requires that the solution stream be segmented, e.g., by air segments, to wash the cell clean from test sample to test sample, as shown in U.S. Pat. No. 3,840,438, assigned to a common assignee. Even with high flow rates, stagnant layers may exist upon the sensing membranes or elements to affect the accuracy of the measurement. These stagnant layers are effectively eliminated by the air segments in the stream as they virtually occlude the flow passage of the cell.

A problem, however, is associated with the passage of occluding air segments in the sample stream flowing through a test cell. In a pH cell, for example, when one or more air segments fill the space between the pH membrane and the porous liquid junction of the reference electrode of the cell, the effective solution resistance greatly increases due to "impedance shock" and "streaming potentials" arise, which degrade the pH measurement. By "streaming potentials" is meant the voltage difference developed along a portion of a conduit through which liquid is flowed because of the flow pattern of the liquid. The liquid flowing through the conduit has a double charge consisting of a fixed layer of charge on the surfaces of the inner wall of the conduit and a counter charged layer partially distributed in the bulk of the solution. A voltage difference in the direction of liquid flow is thus established, and a reverse flow of ionic charge through the liquid will occur. The magnitude of the streaming potential is inversely proportional to the conductance of the solution; and is a function of conduit geometry. By "impedance shock" is meant the sudden increase in solution resistance caused by the inert segment entering between sensing elements in the conduit. This sudden resistance additionally causes a ringing signal (noise) in the potential. In addition, "surging" within the stream itself, further degrades the measurement by introducing oscillations (noise) into the signal. By "surging" is meant that the inert segments, which may be air, are not evenly spaced due to flow abnormalities associated with the insertion of the air into the stream or due to the pumping action driving the solution stream. As a result, reliable ionic measurements using segmented streams are not possible. The degradation is particularly severe when dealing with medium to poorly buffered solutions, which usually exhibit low conductivities. This is true, because the magnitude of the noise increases as a function of decreasing solution conductivity, while the magnitude of the signal is independent of solution conductivity. Signal sampling and averaging techniques could normally be applied to improve the signal-to-noise ratio, but due to the variations in the flow conditions, these techniques are not entirely satisfactory.

The invention seeks to eliminate the aforementioned problems, by reducing the magnitude of the potential drop and noise in the test cell measurement generated by the continuously flowing, air-segmented, weakly conducting solution stream. This is accomplished by inserting a conductive wire down the center or mid-portion of the flow-through cell, which acts as a low-impedance shunt through the fluid, which virtually eliminates the unwanted potentials and noise.

In the aforementioned U.S. Pat. No. 3,840,438, it is taught that ion selective electrodes may be preconditioned to the test solution in order to provide a quicker electrical response, and reduce transient errors. Such error elimination, however, does not direct itself to the above-mentioned problems associated with the inert segments within the solution stream. The solutions contemplated for particular use in the pH cell embodiment described hereinafter, are medium to poorly buffered and of low conductivity. It should be understood, however, that the invention is not limited solely to pH cells, but is useful in all ionic measurements featuring inert segmented solution streams.

SUMMARY OF THE INVENTION

The invention in one embodiment relates to a flow-through pH test cell for determining the pH of medium to weakly buffered, weakly conducting solutions. For example, such solutions can be successive samples in a flowing stream which is passed through the pH cell, adjacent samples being separated by at least one air bubble. The pH cell comprises a pH membrane disposed at a mid-portion of a fluid conduit. The conduit conducts the sample stream past the pH membrane and a spaced porous liquid junction element which acts as a bridge between a reference electrode compartment and the test solution. The air segments in the flowing stream provide a good detergent action upon the walls of the conduit and pH membrane. First and second electrodes, each immersed in standard electrolyte solutions, measure the voltage change indicative of the pH across the pH membrane.

To minimize "impedance shocks" and "streaming potentials" within the cell, an electrical conductor is disposed an extended distance along said conduit to provide a low-impedance path through the portion of the stream disposed between the membrane and liquid junction. The presence of such a low-impedance path improves the signal-to-noise ratio. The conductor has a substantially straight portion and end portions. The straight portion passes adjacent to the pH membrane and the liquid junction element in non-contacting propinquity. The end portions disposed on each end of the element fixedly position the straight portion within the conduit.

It is an object of the invention to provide an improved flow-through test cell;

It is another object of this invention to provide a low-impedance shunt through an inert-segmented fluid of a flow-through test cell;

It is a further object of this invention to provide a flow-through inert-segmented test cell that has an improved signal-to-noise ratio;

It is yet another object of this invention to provide a flow-through inert-segmented ionic cell whose signal is an accurate measurement of ionic activity in medium to weakly buffered, low conductive solutions; and It is still a further object of the invention to provide a flow-through test cell that is relatively unaffected, by "streaming potentials", "impedance shock" and "surging" within the inert-segmented solution under test.

These and other objects of this invention will be better understood and will become more apparent with reference to the following detailed description taken in conjunction with the accompanying drawings in which.

Figure 1:
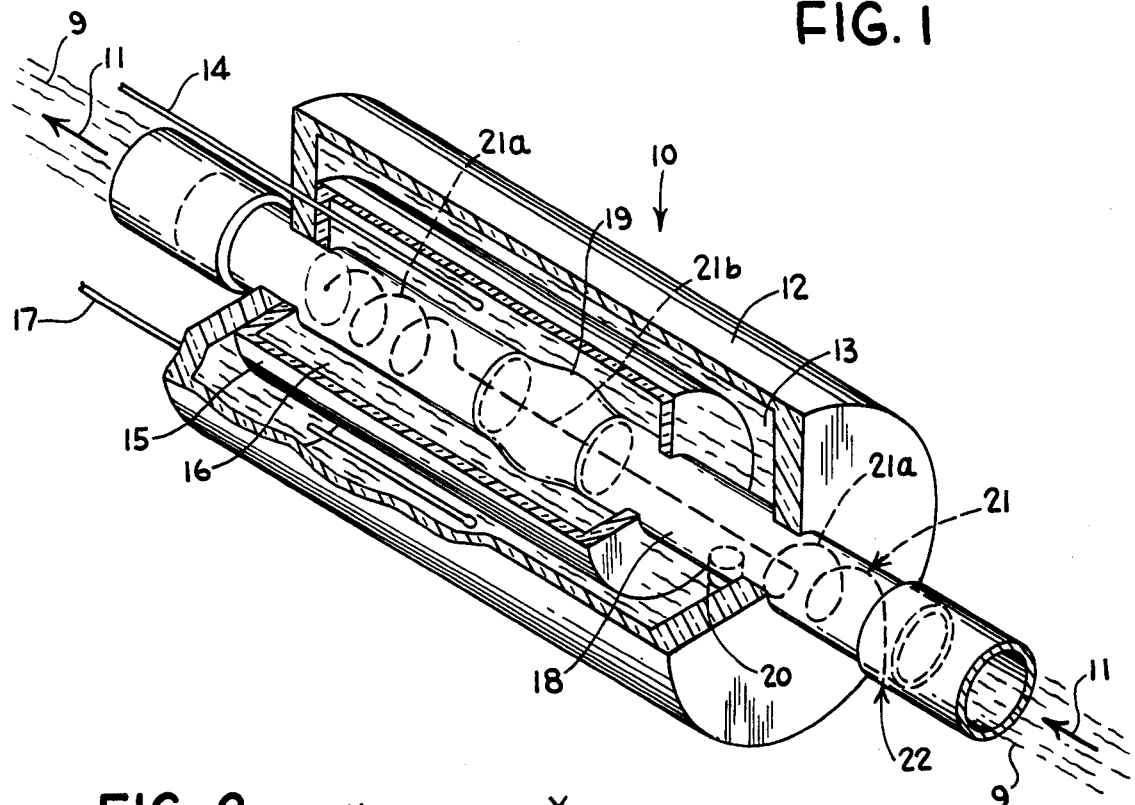
FIG. 1 is a perspective cut-away view of a pH cell of this invention.
Figure 2:
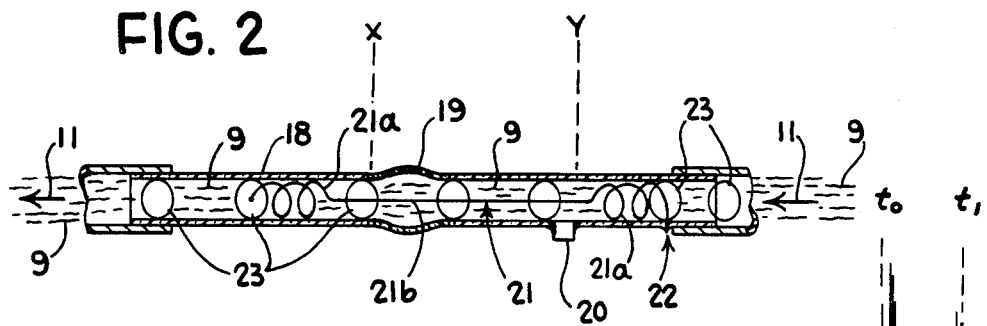
FIG. 2 is a sectional view of the conduit portion of the pH cell of FIG. 1.
Figure 3:
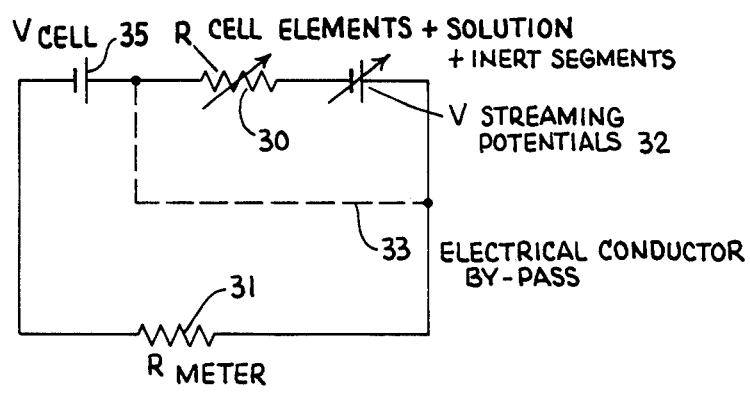
Figure 4:
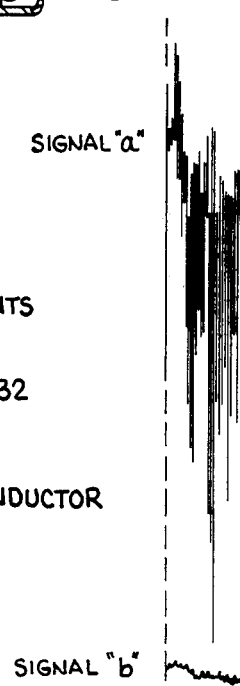

FIG. 3 is a schematic diagram of an analogue circuit for the pH cell of FIG. 1, showing the voltage of the pH cell and associated voltage drops; and FIG. 4 is a typical diagram of the pH signal generated between points "X" and "Y" of FIG. 2, during a measured interval of time $t_1-t_0$: signal (a) with the inert-segmented stream, but without the low-impedance shunt; and signal (b) with the inert-segmented stream and the low-impedance shunt.

DETAILED DESCRIPTION

Generally speaking, the invention is for an improved flow-through test cell for testing ionic activity of a solution. The cell comprises a conduit for conveying the solution as a continuous stream segmented by inert fluid segments. A pair of electrodes associated with the conduit measures the potential of the solution disposed therebetween as a function of the ionic activity. The signal-to-noise ratio of such measurement is improved by the provision of an electrical conductor disposed in the conduit between the measuring electrodes which effectively provides a conductive path in the flowing solution stream. Such conductor acts as a low-impedance shunt across a segmented portion of the solution stream to substantially eliminate the effects of impedance shock due to the passage of inert fluid segments and, also, the effects of surging and streaming potentials developed in the stream. The conductor is fixedly positioned in non-contacting adjacency with the conduit to prevent shorting of the shunted path.

Referring to FIG. 1, a pH cell 10 is shown for testing a solution 9, which may comprise successive fluid samples. The solution 9 passes through the cell 10 as depicted by arrows 11. The pH cell 10 comprises a first outer glass chamber 12 containing a standard electrolyte fluid 13, such as HCl. A first reference electrode 14 extends through the outer glass chamber 12 into fluid 13. Contained inside the outer glass chamber 12 is another glass chamber 15 also containing an electrolyte fluid 16, such as saturated KCl and saturated AgCl. A second reference electrode 17 extends through the walls of chambers 12 and 15 into fluid 16.

A glass conduit 18 extends through the center of the pH cell 10 as illustrated, and conducts the solution 9 under test past a bulb-like pH glass membrane 19 disposed in the mid-portion of the cell 10. A porous ceramic frit 20 is disposed in the conduit 18 and acts as a liquid junction between electrolyte fluid 13 and solution 9.

An electrical conductor 21 of low-impedance is anchored to the glass conduit 18 at point 22. The electrical conductor 21 can be comprised of platinum or stainless steel wire and is comprised of three sections: one substantially straight center section 21b; and two coiled distal sections 21a.

Operation of the pH cell 10 will be explained with reference to FIGS. 2 through 4.

Referring to FIG. 2, solution 9 passed along the conduit 18 is segmented with inert segments 23, e.g., air, which are evenly spaced. The air segments 23 are introduced into the solution 9 upstream of the cell 10, as described in U.S. Pat. No. 3,840,438. Preferably, the bubbles 23 are evenly spaced within solution 9. During measurement, portions of solution 9 between frit 20 and membrane 19, albeit separated by successive air segments 23, would comprise a particular sample to be measured. However, due to surges in the flow of solution 9 due to the pumping action and other flow abnormalities, the air segments 23 usually have an uneven or staggered pattern within the solution 9. FIG. 2 is an exaggerated view of the staggering of the air segments 23. The air segments 23 serve the purpose of cleaning the surface of conduit 18, frit 20 and pH membrane 19 of stagnant layers of fluid, that act to give erroneous pH readings. It is most important to clear these "dead" layers of fluid from the cell 10 to avoid contamination between successive samples. The air bubbles 23 act to rid the cell of this contamination.

However, the segmentation of solution 9 introduces a problem with measuring the pH signal. This problem can best be understood by making reference to FIGS. 3 and 4. The signal "a" in FIG. 4 represents the measured pH potential generated between points "X" and "Y" of FIG. 2 during a measured interval of time $t_1-t_0$. Signal "a" shows the distortion introduced into the signal during the measuring cycle by an inert segment interrupting the conductive path between frit 20 and membrane 19. With the conductor 21 in place, such conductive path is defined between membrane 19 and through solution 9 to conductor 21 and along such conductor to and through the solution to frit 20. It is evident that the effective conductive path is defined by that volume of solution 9 between conductor 21 and membrane 19 and frit 20, respectively. Accordingly, the effective conductive path is interrupted whenever an air bubble is positioned over either membrane 19 and frit 20 and, also, exaggerates the effects of the streaming potential introduced between membrane 19 and frit 20. The inert segment 23, as it is exhibits a much higher impedance than solution 9, introduces an impedance shock which substantially increases the potential drop between the frit 20 and the pH membrane 19 (FIGS. 1 and 2).

FIG. 3 shows an equivalent electrical circuit for the pH cell 10 of FIGS. 1 and 2. As will be seen from this figure, the cell may be described as a voltage source 35. A variable resistance 30 represents the impedance associated with electrodes 14 and 17, the electrolytes 13 and 16, the conductivity of solution 9 and the inert segments 23, etc. It should be appreciated that the variability of resistance 30 results from the presence or absence of an air bubble between membrane 19 and frit 20. Another source of variable potential in cell 10 results from a "streaming potential", illustrated as variable potential source 32 which is the result of a thin stagnant layer of charge that coats the surface of conduit 18 between the frit 20 and pH membrane 19. This "streaming potential"

is continuously changing with the changing flow conditions and solution conductivity.

The inherent impedance of the potential measuring pH meter (not shown) is represented by resistance 31 and should be large compared to the other resistances for purposes of obtaining reproducible and accurate measurements. The resistance 31 becomes part of the cell circuit when it is switched on to measure the pH. Insertion of the electrical conductor 21b between membrane 19 and frit 20 of FIGS. 1 and 2, effectively forms a low-impedance by-pass of variable resistance 30 and the variable potential source 32, as shown by the dotted line 33 in FIG. 3. This by-pass 33 effectively eliminates the aforementioned distortion in the pH measurement signal between points "X" and "Y" (FIG. 2) as shown by signal "b" in FIG. 4. As is evident, the signal-to-noise ratio has been greatly improved, such that a measurable pH signal is now obtainable even with solutions of very low ionic activity.

In order that wire 21 be effective, however, it is further necessary to make sure that the wire 21 does not touch the sides of the conduit along its straight section 21b. To achieve this, the invention seeks to anchor the wire in place at point 22, and position the section 21b by means of distal sections 21a. Thus, that the wire 21b is fixedly secured and in a non-contacting adjacency to the pH membrane 19 and the frit 20.

Having described the invention, what is sought to be protected by Letters Patent is presented by the following appended claims.

What is claimed is:

1. A flow-through test cell for testing an ionic activity of a solution including a conduit for conveying said solution in a stream segmented by inert fluid segments, and a pair of spaced electrodes in association with said conduit for measuring the ionic activity of one or more segments of said solution being conveyed therebetween, an improvement comprising an electrical conductor disposed within said conduit and extending, at least, between said spaced electrodes for improving the signal-to-noise ratio; and means for fixedly positioning said electrical conductor within said solution stream in non-contacting adjacency with said electrodes.

2. The flow-through test cell of claim 1, wherein said electrical conductor is a wire having a substantially straight section extending at least between said electrodes and said positioning means comprises end portions of said electrical conductor for fixedly positioning said straight wire section centrally within said conduit.

3. The flow-through test cell of claim 2, wherein said end portions are coil-shaped.

4. The flow-through test cell of claim 2, wherein said conduit is comprised of a glass wall, and said positioning means includes means for anchoring at least one of said end portions into said glass wall of said conduit.

5. The flow-through test cell of claim 1, wherein said electrical conductor extends beyond said spaced electrodes.

6. The flow-through test cell of claim 1, wherein said cell comprises means for measuring the pH of said solution.

7. The flow-through test cell of claim 1, wherein said positioning means includes means for anchoring at least one end-portion of said electrical conductor into a wall of said conduit.

8. The flow-through test cell of claim 1, wherein said electrical conductor is comprised of stainless steel.

9. The flow-through test cell of claim 1, wherein said electrical conductor is comprised of platinum.

10. The flow-through test cell of claim 1, wherein said electrical conductor is comprised of a chemically inert material.

11. A flow-through ionic cell, comprising:
a conduit for conducting a solution as a stream separated by inert fluid segments;
a first electrode means comprising an ionic sensing electrode associated with said conduit;
a second electrode means comprising a liquid junction in fluid communication with said conduit and spaced-apart from said sensing electrode;
an electrical conductor disposed along said conduit and extended at least between said sensing electrode and said liquid junction for providing a low-impedance path to improve signal-to-noise ratio, said electrical conductor having a substantially straight portion in non-contacting relationship to said sensing electrode and said liquid junction, said electrical conductor having an end portion fixedly positioning said straight portion within said conduit.

12. The flow-through ionic cell in accordance with claim 11, wherein said ionic sensing electrode has a length which is longer than any of said inert fluid segments.

13. The flow-through ionic cell in accordance with claim 11, wherein said end portion is coil-shaped.

14. The flow-through ionic cell in accordance with claim 11, wherein said electrical conductor has a second end portion cooperating to fixedly position said electrical conductor.

15. The flow-through ionic cell in accordance with claim 14, wherein each of said first and second end portions are coil-shaped.

16. The flow-through ionic cell in accordance with claim 11, wherein said electrical conductor comprises a substantially chemically inert material.

17. The flow-through ionic cell in accordance with claim 16, wherein said chemically inert material comprises platinum.

18. The flow-through ionic cell in accordance with claim 16, wherein said chemically inert material comprises stainless steel.

19. The flow-through ionic cell in accordance with claim 11, wherein said sensing electrode is a pH membrane.

20. The flow-through ionic cell in accordance with claim 19, wherein said pH membrane is disposed within a mid-portion of said conduit and has an annular bulb-like shape.

21. The flow-through ionic cell in accordance with claim 11, wherein said liquid junction comprises a frit disposed flush with an inner wall of said conduit.

* * * * *